US011118661B2

(12) United States Patent
Abbott

(10) Patent No.: US 11,118,661 B2
(45) Date of Patent: Sep. 14, 2021

(54) INSTRUMENT TRANSMISSION CONVERTING ROLL TO LINEAR ACTUATION

(71) Applicant: Intuitive Surgical Operations, Inc., Sunnyvale, CA (US)

(72) Inventor: Ryan C. Abbott, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 68 days.

(21) Appl. No.: 16/271,251

(22) Filed: Feb. 8, 2019

(65) Prior Publication Data
US 2019/0249759 A1    Aug. 15, 2019

Related U.S. Application Data

(60) Provisional application No. 62/629,188, filed on Feb. 12, 2018.

(51) Int. Cl.
*F16H 21/44*   (2006.01)
*B25J 9/10*   (2006.01)
(Continued)

(52) U.S. Cl.
CPC ............. *F16H 21/44* (2013.01); *A61B 34/30* (2016.02); *A61B 34/35* (2016.02); *B25J 9/10* (2013.01);
(Continued)

(58) Field of Classification Search
CPC ........ B25J 9/1689; B25J 9/107; B25J 9/1065; B25J 9/106; B25J 9/12; B25J 9/123;
(Continued)

(56) References Cited

U.S. PATENT DOCUMENTS

| 793,510 A | 6/1905 | Cramer et al. |
| 2,906,143 A | 9/1959 | Musser |
| (Continued) | | |

FOREIGN PATENT DOCUMENTS

| CN | 2573759 Y | 9/2003 |
| JP | H06114000 A | 4/1994 |
| (Continued) | | |

OTHER PUBLICATIONS

Litvin F.L., et al., "Face Gear Drive with Helical Involute Pinion: Geometry, Generation by a Shaper and a Worm, Avoidance of Singularities and Stress Analysis," NASA/CR-2005-213443, ARL-CR-557, Feb. 2005, 62 pages.

(Continued)

*Primary Examiner* — Daniel D Yabut

(57) ABSTRACT

A force transmission mechanism includes a chassis that supports a rotatable arm, which includes a slot. A rotatable lever is supported by the chassis. A protrusion at an end of the lever engages the slot. A sliding drive element is supported by the chassis. A proximal termination of the drive element engages a second end of the lever. The chassis may support an elongate tube with an end effector fixed to the tube. The drive element may extend through the elongate tube. The elongate tube may rotate relative to the chassis. The drive element may rotate in unison with the elongate tube with the proximal termination rotating relative to the fork. The drive element may be a tube that provides a fluid passage to the end effector. The lever may be a bell crank with arms at a right angle.

20 Claims, 9 Drawing Sheets

(51) Int. Cl.
  *B25J 9/16* (2006.01)
  *A61B 34/35* (2016.01)
  *A61B 34/30* (2016.01)
  *A61B 18/14* (2006.01)
  *A61B 17/00* (2006.01)

(52) U.S. Cl.
  CPC ......... *B25J 9/1689* (2013.01); *A61B 18/1445* (2013.01); *A61B 2017/00477* (2013.01); *A61B 2218/002* (2013.01)

(58) Field of Classification Search
  CPC .... B25J 9/126; B25J 15/0028; B25J 15/0206; B25J 15/0213; B25J 15/022; B25J 15/0226; B25J 15/0266; B25J 15/0273; B25J 15/028; B25J 15/0253; B25J 15/024; B25J 15/0293; B25J 9/10; Y10T 74/18248; Y10T 74/18256; Y10T 74/18208; Y10T 74/18216; Y10T 74/182; Y10T 74/18184; Y10T 74/18176; A61B 34/35; F16H 21/44; F16H 21/40; F16H 21/48–54
  See application file for complete search history.

(56) References Cited

U.S. PATENT DOCUMENTS

| | | | |
|---|---|---|---|
| 3,312,496 A * | | 4/1967 | Boutelle ............ B25J 17/0241 294/66.1 |
| 4,139,104 A * | | 2/1979 | Mink ................ B25J 15/02 414/744.8 |
| 4,243,257 A * | | 1/1981 | Shackleford ........... B25J 15/02 294/103.1 |
| 4,540,211 A * | | 9/1985 | Masserang ........... B25J 15/103 294/115 |
| 4,705,311 A * | | 11/1987 | Ragard ............... B23P 19/007 294/2 |
| 4,728,137 A * | | 3/1988 | Hamed .............. B25J 15/0266 269/228 |
| 4,899,608 A | | 2/1990 | Knappe et al. |
| 5,099,705 A * | | 3/1992 | Dravnieks ............ B23D 51/02 30/392 |
| 5,674,024 A | | 10/1997 | Daumal et al. |
| 5,792,135 A | | 8/1998 | Madhani et al. |
| 5,807,377 A | | 9/1998 | Madhani et al. |
| 5,876,325 A | | 3/1999 | Mizuno et al. |
| 6,007,550 A | | 12/1999 | Wang et al. |
| 6,318,199 B1 | | 11/2001 | Buck |
| 6,331,181 B1 | | 12/2001 | Tierney et al. |
| 6,371,952 B1 | | 4/2002 | Madhani et al. |
| 6,394,998 B1 | | 5/2002 | Wallace et al. |
| 6,817,974 B2 | | 11/2004 | Cooper et al. |
| 6,994,708 B2 | | 2/2006 | Manzo et al. |
| 6,997,079 B2 | | 2/2006 | Nomura et al. |
| 7,090,683 B2 | | 8/2006 | Brock et al. |
| 7,169,141 B2 | | 1/2007 | Brock et al. |
| 7,214,230 B2 | | 5/2007 | Brock et al. |
| 7,331,967 B2 | | 2/2008 | Lee et al. |
| 7,371,210 B2 | | 5/2008 | Brock et al. |
| 7,524,320 B2 | | 4/2009 | Tierney |
| 7,666,191 B2 | | 2/2010 | Orban, III et al. |
| 7,935,130 B2 | | 5/2011 | Williams et al. |
| 8,316,961 B2 | | 11/2012 | Isobe et al. |
| 8,444,631 B2 | | 5/2013 | Yeung et al. |
| 8,479,969 B2 | | 7/2013 | Shelton, IV et al. |
| 8,506,555 B2 | | 8/2013 | Ruiz et al. |
| 8,551,115 B2 | | 10/2013 | Steger et al. |
| 8,597,280 B2 | | 12/2013 | Cooper et al. |
| 8,771,270 B2 | | 7/2014 | Burbank et al. |
| 8,800,838 B2 | | 8/2014 | Shelton, IV et al. |
| 8,992,565 B2 | | 3/2015 | Brisson et al. |
| 9,028,494 B2 | | 5/2015 | Shelton, IV et al. |
| 9,078,684 B2 | | 7/2015 | Williams et al. |
| 9,121,494 B2 | | 9/2015 | Buchleitner et al. |
| 9,204,923 B2 | | 12/2015 | Manzo et al. |
| 9,232,979 B2 | | 1/2016 | Parihar et al. |
| 9,259,274 B2 | | 2/2016 | Prisco et al. |
| 9,289,112 B2 | | 3/2016 | Takemoto et al. |
| 9,664,262 B2 * | | 5/2017 | Donlon ................ F16H 19/001 |
| 9,737,373 B2 | | 8/2017 | Schuh et al. |
| 9,839,439 B2 | | 12/2017 | Cooper et al. |
| 9,931,106 B2 | | 4/2018 | Au et al. |
| 9,993,313 B2 | | 6/2018 | Schuh et al. |
| 10,016,244 B2 | | 7/2018 | Cooper et al. |
| 10,022,193 B2 | | 7/2018 | Cooper et al. |
| 10,076,348 B2 | | 9/2018 | Anderson et al. |
| 1,013,036 A1 | | 11/2018 | Shelton, IV et al. |
| 10,201,365 B2 | | 2/2019 | Boudreaux et al. |
| 10,219,874 B2 | | 3/2019 | Yu et al. |
| 10,470,830 B2 | | 11/2019 | Hill et al. |
| 10,595,949 B2 | | 3/2020 | Donlon et al. |
| 10,653,489 B2 | | 5/2020 | Kopp |
| 10,667,877 B2 | | 6/2020 | Kapadia |
| 10,682,141 B2 | | 6/2020 | Moore et al. |
| 10,881,280 B2 | | 1/2021 | Baez, Jr. |
| 10,932,868 B2 | | 3/2021 | Solomon et al. |
| 2002/0111635 A1 | | 8/2002 | Jensen et al. |
| 2005/0042943 A1 | | 2/2005 | Mocivnik et al. |
| 2005/0089345 A1 | | 4/2005 | Yasumoto et al. |
| 2005/0119527 A1 | | 6/2005 | Banik et al. |
| 2007/0043338 A1 | | 2/2007 | Moll et al. |
| 2007/0232858 A1 | | 10/2007 | MacNamara et al. |
| 2008/0046122 A1 | | 2/2008 | Manzo et al. |
| 2008/0065102 A1 | | 3/2008 | Cooper et al. |
| 2008/0065105 A1 | | 3/2008 | Larkin et al. |
| 2008/0087871 A1 | | 4/2008 | Schena et al. |
| 2008/0103491 A1 | | 5/2008 | Omori et al. |
| 2008/0196533 A1 | | 8/2008 | Bergamasco et al. |
| 2009/0088774 A1 | | 4/2009 | Swarup et al. |
| 2009/0198272 A1 | | 8/2009 | Kerver et al. |
| 2010/0011900 A1 | | 1/2010 | Burbank et al. |
| 2010/0170519 A1 | | 7/2010 | Romo et al. |
| 2010/0175701 A1 | | 7/2010 | Reis et al. |
| 2010/0318101 A1 | | 12/2010 | Choi et al. |
| 2011/0015650 A1 | | 1/2011 | Choi et al. |
| 2011/0118754 A1 | | 5/2011 | Dachs, II et al. |
| 2011/0277775 A1 | | 11/2011 | Holop et al. |
| 2011/0295269 A1 | | 12/2011 | Swensgard et al. |
| 2011/0295270 A1 | | 12/2011 | Giordano et al. |
| 2012/0046522 A1 | | 2/2012 | Naito |
| 2012/0123441 A1 | | 5/2012 | Au et al. |
| 2012/0239060 A1 | | 9/2012 | Orban, III et al. |
| 2012/0289974 A1 | | 11/2012 | Rogers et al. |
| 2012/0298719 A1 | | 11/2012 | Shelton et al. |
| 2013/0046318 A1 | | 2/2013 | Radgowski et al. |
| 2013/0123783 A1 | | 5/2013 | Marczyk et al. |
| 2013/0144395 A1 | | 6/2013 | Stefanchik et al. |
| 2014/0005662 A1 | | 1/2014 | Shelton, IV |
| 2014/0005678 A1 | | 1/2014 | Shelton, IV et al. |
| 2014/0005708 A1 | | 1/2014 | Shelton |
| 2014/0100558 A1 | | 4/2014 | Schmitz et al. |
| 2014/0114327 A1 | | 4/2014 | Boudreaux et al. |
| 2014/0257333 A1 | | 9/2014 | Blumenkranz |
| 2014/0276723 A1 | | 9/2014 | Parihar et al. |
| 2014/0309625 A1 | | 10/2014 | Okamoto et al. |
| 2015/0051034 A1 | | 2/2015 | Cooper et al. |
| 2015/0150635 A1 | | 6/2015 | Kilroy et al. |
| 2015/0150636 A1 | | 6/2015 | Hagn et al. |
| 2015/0157355 A1 | | 6/2015 | Price et al. |
| 2016/0058443 A1 | | 3/2016 | Yates et al. |
| 2016/0151115 A1 | | 6/2016 | Karguth et al. |
| 2016/0184034 A1 | | 6/2016 | Holop et al. |
| 2016/0184036 A1 | | 6/2016 | Solomon et al. |
| 2016/0184037 A1 | | 6/2016 | Cooper et al. |
| 2016/0199138 A1 | | 7/2016 | Cooper et al. |
| 2016/0296219 A1 | | 10/2016 | Srivastava et al. |
| 2016/0361049 A1 | | 12/2016 | Dachs, II et al. |
| 2017/0007345 A1 | | 1/2017 | Smith et al. |
| 2017/0022754 A1 * | | 1/2017 | Nien ................ E06B 9/307 |
| 2017/0027656 A1 | | 2/2017 | Robert et al. |
| 2017/0165017 A1 | | 6/2017 | Chaplin et al. |
| 2018/0055583 A1 | | 3/2018 | Schuh et al. |

(56) References Cited

U.S. PATENT DOCUMENTS

| | | |
|---|---|---|
| 2018/0229021 A1 | 8/2018 | Donlon et al. |
| 2018/0243036 A1 | 8/2018 | Donlon et al. |
| 2019/0099227 A1 | 4/2019 | Rockrohr |
| 2019/0125468 A1 | 5/2019 | Adams |
| 2019/0192137 A1 | 6/2019 | Shelton et al. |
| 2019/0223960 A1 | 7/2019 | Chaplin et al. |
| 2019/0231451 A1 | 8/2019 | Lambrecht et al. |
| 2019/0231464 A1 | 8/2019 | Wixey et al. |
| 2019/0239965 A1 | 8/2019 | Abbott |
| 2019/0298323 A1 | 10/2019 | Lambrecht et al. |
| 2019/0307522 A1 | 10/2019 | Lambrecht et al. |
| 2019/0328467 A1 | 10/2019 | Waterbury et al. |
| 2020/0093554 A1 | 3/2020 | Schuh et al. |
| 2020/0197117 A1 | 6/2020 | Donlon et al. |

FOREIGN PATENT DOCUMENTS

| | | |
|---|---|---|
| JP | H10249777 A | 9/1998 |
| JP | 2003024336 A | 1/2003 |
| JP | 2005288590 A | 10/2005 |
| WO | WO-9729690 A1 | 8/1997 |
| WO | WO2009/039506 A1 | 3/2009 |
| WO | WO2012/068156 A2 | 5/2012 |
| WO | WO2012/166806 A1 | 12/2012 |
| WO | WO-2015142290 A1 | 9/2015 |
| WO | WO-2016073637 A1 | 5/2016 |
| WO | WO-2016161449 A1 | 10/2016 |
| WO | WO-2016172299 A1 | 10/2016 |
| WO | WO-2016189284 A1 | 12/2016 |
| WO | WO-2017188851 A1 | 11/2017 |
| WO | WO-2018013313 A1 | 1/2018 |
| WO | WO2018/049217 A1 | 3/2018 |
| WO | WO-2018094191 A1 | 5/2018 |
| WO | WO2020/102776 A1 | 5/2020 |

OTHER PUBLICATIONS

Litvin F.L., et al., "Handbook on Face Gear Drives with a Spur Involute Pinion," NASA/CR-2000-209909, ARL-CR-447, Mar. 2000, 106 pages.

Smith L.J., "The Involute Helicoid and the Universal Gear," Gear Technology, Nov./Dec. 1990, pp. 18-27.

Stadtfeld H, Dr., "Tribology Aspects in Angular Transmission Systems: Part I—General Explanations on Theoretical Bevel Gear Analysis," Gear Technology, Aug. 2010, URL: https://www.geartechnology.com/issues/0810x/stadtfeld1.pdf, pp. 46-52.

Stadtfeld H, Dr., "Tribology Aspects in Angular Transmission Systems: Part II—Straight Bevel Gears," Gear Technology, Sep.-Oct. 2010, URL: http://www.geartechnology.com/issues/0910x/stadtfeld.pdf, pp. 47-52.

Stadtfeld H, Dr., "Tribology Aspects in Angular Transmission Systems: Part III—Zerol Bevel Gears," Gear Technology, Nov.-Dec. 2010, URL: http://www.geartechnology.com/issues/1110x/zerol.pdf, pp. 42-47.

Stadtfeld H, Dr., "Tribology Aspects in Angular Transmission Systems: Part IV—Spiral Bevel Gears," Gear Technology, Jan.-Feb. 2011, URL: https://www.geartechnology.com/issues/0111x/stadtfeld.pdf, pp. 66-72.

Stadtfeld H, Dr., "Tribology Aspects in Angular Transmission Systems: Part V—Face Gears," Gear Technology, Mar.-Apr. 2011, URL: http://www.geartechnology.com/issues/0311x/stadtfeld.pdf, pp. 47-52.

Stadtfeld H, Dr., "Tribology Aspects in Angular Transmission Systems: Part VI—Beveloid & Hypoloid Gears," Gear Technology, May 2011, URL: https://www.geartechnology.com/issues/0511x/beveloid.pdf, pp. 48-52.

Stadtfeld H, Dr., "Tribology Aspects in Angular Transmission Systems: Part VII—Hypoid Gears," Gear Technology, Jun.-Jul. 2011, URL: https://www.geartechnology.com/issues/0611x/hypoid.pdf, pp. 66-72.

Stadtfeld H, Dr., "Tribology Aspects in Angular Transmission Systems: Part VIII—Super-Reduction Hypoid Gears," Gear Technology, Aug. 2011, URL: http://www.geartechnology.com/issues/0811x/superhypoid.pdf, pp. 42-48.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

INSTRUMENT TRANSMISSION CONVERTING ROLL TO LINEAR ACTUATION

RELATED APPLICATION

This patent application claims priority to and the filing date benefit of U.S. Provisional Patent Application No. 62/629,188 (filed Feb. 12, 2018) (entitled "INSTRUMENT TRANSMISSION CONVERTING ROLL TO LINEAR ACTUATION"), which is incorporated by reference herein in its entirety.

FIELD

Embodiments of the invention relate to the field of mechanical couplers; and more specifically, to a mechanical coupler for transferring motion from a teleoperated actuator to an attached surgical instrument.

BACKGROUND

Minimally invasive medical techniques have been used to reduce the amount of extraneous tissue which may be damaged during diagnostic or surgical procedures, thereby reducing patient recovery time, discomfort, and deleterious side effects. Traditional forms of minimally invasive surgery include endoscopy. One of the more common forms of endoscopy is laparoscopy, which is minimally invasive inspection or surgery within the abdominal cavity. In traditional laparoscopic surgery, a patient's abdominal cavity is insufflated with gas, and cannula sleeves are passed through small (approximately 12 mm) incisions in the musculature of the patient's abdomen to provide entry ports through which laparoscopic surgical instruments can be passed in a sealed fashion.

The laparoscopic surgical instruments generally include a laparoscope for viewing the surgical field and surgical instruments having end effectors. Typical surgical end effectors include clamps, graspers, scissors, staplers, and needle holders, for example. The surgical instruments are similar to those used in conventional (open) surgery, except that the working end or end effector of each surgical instrument is separated from its handle by an approximately 30 cm. long extension tube, for example, so as to permit the operator to introduce the end effector to the surgical site and to control movement of the end effector relative to the surgical site from outside a patient's body.

In order to provide improved control of the working tools, it is desirable to control the surgical instrument with teleoperated actuators. The surgeon may operate controls on a computer-assisted control unit to indirectly manipulate the instrument that is connected to the teleoperated actuators. The surgical instrument is detachably coupled to the teleoperated actuators so that the surgical instrument can be separately sterilized, and so that different instruments may be selected for use as needed for the surgical procedure to be performed. The surgical instrument may be changed during the course of a surgery.

It will be appreciated that it is desirable to minimize the diameter of the extension tube, which couples the end effector to the teleoperated actuators, to minimize the size of the incision necessary to introduce the surgical instrument to the surgical site. A teleoperated surgical instrument may have various drive elements that transfer the forces of the teleoperated actuators from a proximal control mechanism at a proximal end of the extension tube to the end effector at a distal end of the extension tube. The drive element may provide push, pull, or push-pull forces to the end effector. The extension tube and the drive element may be rotated together about the longitudinal axis of the extension tube to rotate the end effector.

Rotary actuators, such as electric motors, are an effective way to provide controlled actuation forces to a teleoperated surgical instrument. The instrument's proximal control mechanism translates the rotary input force into the push-pull motions of the drive element needed to control the end effector. The proximal control mechanism may receive one rotary input to control the push-pull motions and a second rotary input to control the rotation of the extension tube and the end effector. It is desirable that the proximal control mechanism be compact to avoiding crowding in the surgical field.

In view of the above, it is desirable to provide an improved apparatus and method for transmitting rotary actuating forces to a push-pull drive element in an elongate tube of a surgical instrument intended for use in teleoperated minimally invasive surgeries.

SUMMARY

A force transmission mechanism includes a chassis that supports a rotatable arm, and the arm includes a slot. A rotatable lever is also supported by the chassis. A protrusion at an end of the lever engages the slot. A sliding drive element is supported by the chassis. A proximal termination of the drive element engages a second end of the lever. The chassis supports an elongate tube with an end effector fixed to the tube. The drive element extends through the elongate tube. The elongate tube may optionally rotate relative to the chassis. The drive element may rotate in unison with the elongate tube with the proximal termination rotating relative to the fork. The drive element may optionally be a tube that provides a fluid passage to the end effector. The lever may optionally be a bell crank with arms at a right angle.

Other features and advantages of the present invention will be apparent from the accompanying drawings and from the detailed description that follows below.

BRIEF DESCRIPTION OF THE DRAWINGS

The invention may best be understood by referring to the following description and accompanying drawings that are used to illustrate embodiments of the invention by way of example and not limitation. In the drawings, in which like reference numerals indicate similar elements.

DESCRIPTION OF EMBODIMENTS

Figure 1:
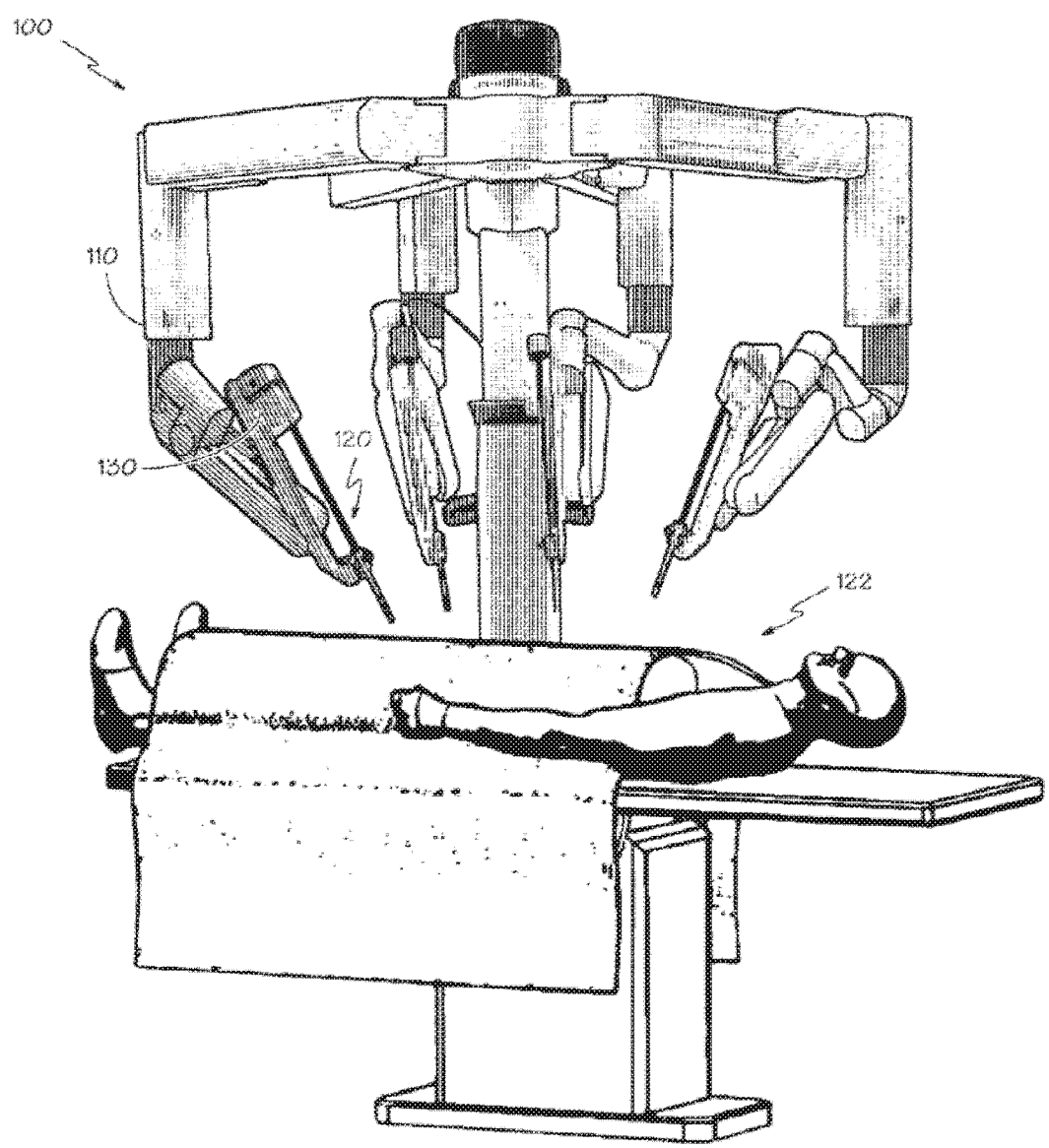
FIG. 1 is a view of an illustrative manipulating system of a teleoperated surgical system.

In the following description, numerous specific details are set forth. However, it is understood that embodiments of the invention may be practiced without these specific details. In other instances, well-known circuits, structures, and techniques have not been shown in detail in order not to obscure the understanding of this description.

In the following description, reference is made to the accompanying drawings, which illustrate several embodiments of the present invention. It is understood that other embodiments may be utilized, and mechanical compositional, structural, electrical, and operational changes may be made without departing from the spirit and scope of the present disclosure. The following detailed description is not to be taken in a limiting sense, and the scope of the embodiments of the present invention is defined only by the claims of the issued patent.

The terminology used herein is for the purpose of describing particular embodiments only and is not intended to be limiting of the invention. Spatially relative terms, such as "beneath", "below", "lower", "above", "upper", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a," "an," and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

The terms "or" and "and/or" as used herein are to be interpreted as inclusive, meaning any one item in a group or any combination of items in the group. Therefore, "A, B, or C" or "A, B, and/or C" mean "any of the following: A; B; C; A and B; A and C; B and C; A, B and C." An exception to this definition will occur only when a combination of elements, functions, steps or acts are in some way inherently mutually exclusive.

The term "object" generally refers to a component or group of components. For example, an object may refer to either a pocket or a boss of a disk within the specification or claims. Throughout the specification and claims, the terms "object," "component," "portion," "part," and "piece" are used interchangeably.

The terms "instrument" and "surgical instrument" are used herein to describe a medical device configured to be inserted into a patient's body and used to carry out surgical or diagnostic procedures. The surgical instrument typically includes an end effector associated with one or more surgical tasks, such as a forceps, a needle driver, a shears, a bipolar cauterizer, a tissue stabilizer or retractor, a clip applier, an anastomosis device, an imaging device (e.g., an endoscope or ultrasound probe), and the like. Some instruments used with embodiments of the invention further provide an articulated support (sometimes referred to as a "wrist") for the surgical end effector so that the position and orientation of the surgical end effector can be manipulated with one or more mechanical degrees of freedom in relation to the instrument's shaft or chassis. Further, many surgical end effectors include one or more functional mechanical degrees of freedom, such as one or more jaws that open or close, or a knife that translates along a path.

FIG. 1 shows a pictorial view of a portion of a minimally invasive teleoperated surgical system. The portion shown is placed adjacent a surgical patient 122 to support the surgical instruments and provide teleoperated actuators that control the surgical instruments. This portion of the teleoperated surgical system may be termed a manipulating system 100. Typically, three or four surgical instruments 120, including a camera instrument that provides images of the surgical site and other instruments at the surgical site, are supported by the manipulating system 100. It will be appreciated that a minimally invasive teleoperated surgical system uses a substantial amount of equipment located in a small amount of space adjacent the surgical patient 122. While the manipulating system 100 is shown as providing four surgical instrument manipulators 130, other numbers of surgical instrument manipulators may be provided, such as one, two, three, or more than four. In some configurations, the teleoperated surgical system may include more than manipulating system. Examples of manipulating systems are included in the da Vinci® Surgical System Models IS1200, IS2000, IS3000, and IS4000 commercialized by Intuitive Surgical, Inc., Sunnyvale, Calif. Manipulating systems include various ways in which they may be mechanically grounded, such as a cart that rolls on the floor, a ceiling mount, a patient operating table mount, and the like. An example of how a manipulating system may be combined with the operating table, are the manipulators and manipulator positioning arms used for the Zeus® Surgical System commercialized by Computer Motion, Inc. and shown, for example, in U.S. Pat. No. 6,728,599 B2 (filed Sep. 7, 2001).

In practice, a manipulator 130 may move the surgical instrument 120 as a whole, and it may also transmit force to the instrument to move one or more instrument components, such as a wrist or jaw mentioned above. In the example shown, the teleoperated surgical instruments 120 are each coupled to a corresponding instrument carriage on a manipulator 130. The instrument carriage houses the teleoperated actuators that provide the mechanical power that is transmitted to the instrument. In some configurations, the teleoperated actuators are housed elsewhere in the manipulator or in a supporting arm. The teleoperated actuators allow a surgeon to manipulate the surgical instrument by using a computer-operated user control station (not shown) that provides computer-assisted teleoperation. These manipulations may include functions such as changing the position and orientation of the surgical instrument's end effector and operating the end effector, such as closing jaws to effect grasping, cutting, etc. Such actuator control of surgical instruments may be referred to by various terms, such as teleoperated surgery. Each manipulator 130 may be supported on a separate supporting arm 110 that, once positioned, can be fixed relative to the surgical patient 122. In various implementations the supporting arm 110 may be manually positioned, may be positioned via teleoperation by the surgeon, or may be automatically positioned by the system as the surgeon moves one or more of the surgical instruments 120.

A control system couples the computer-assisted user control station to the teleoperated actuators. Here "computer" broadly encompasses a data processing unit that incorporates a memory and an additive or logical function, such as an arithmetic logic unit, that is programmable to perform arithmetic or logical operations. The computer-assisted user control station includes one or more hand-operated control input devices that allow manipulation of the teleoperated surgical instruments 120 by transmitting signals, such as electrical or optical control signals, to the actuators that control the actions of the coupled teleoperated surgical instruments. In this way a master-slave relationship is established between the control input device of the user control station and the surgical instrument of the manipulating system.

The hand-operated control input devices, and the images of the surgical site and instruments at the surgical site provided by a camera instrument, may be arranged to provide an intuitive control of the surgical instruments 120, in which the instruments move in a manner similar to the operator's hand movements with the controllers. The movement of the surgical instruments 120 as displayed to the surgeon may appear at least substantially connected to the input devices in the hands of the surgeon. Further levels of connection, such as force or other haptic feedback, may be provided to enhance the surgeon's dexterity and ease of use of the surgical instruments 120. One, two, three, or more actuators may be provided to move the end effector of the associated surgical instrument 120 with one or more mechanical degrees of freedom (e.g., all six Cartesian degrees of freedom, five or fewer Cartesian degrees of freedom, jaw grip, etc.).

Figure 2:
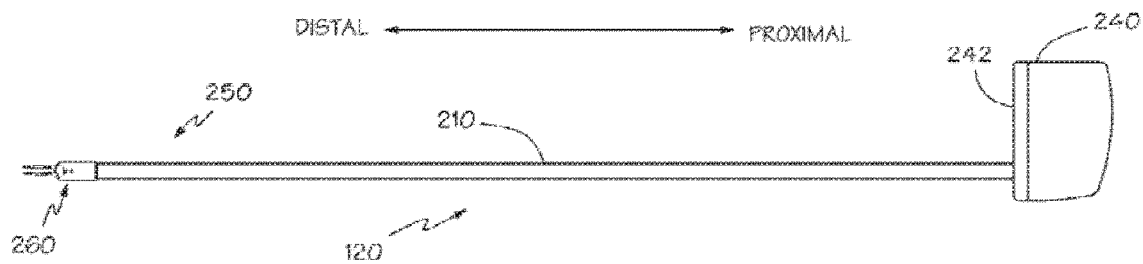
FIG. 2 is a side view of a surgical instrument for use with a teleoperated actuator.

FIG. 2 is a side view of an illustrative embodiment of the surgical instrument 120, comprising a distal portion 250 and a proximal control mechanism 240 coupled by an elongate tube 210. The distal portion 250 of the surgical instrument 120 may provide any of a variety of surgical end effectors 260, such as the forceps shown, a needle driver, a cautery device, a surgical stapler, a cutting tool, an imaging device (e.g., an endoscope or ultrasound probe), or a combined device that includes a combination of two or more various tools and imaging devices. The tube 210 may rotate around its long axis so that the end effector 260 correspondingly rolls around its long axis. The end effector and its components illustrate various movable distal components of the surgical instrument.

Surgical instruments that incorporate inventive aspects control their end effectors with a drive element, such as a rod or tube or other element capable of transmitting push, pull, or push-pull motion (e.g., Bowden cables, etc.). The drive element extends from the proximal control mechanism 240 to the surgical end effectors 260 through the elongate tube 210. A typical elongate tube 210 for a surgical instrument 120 is small, often in a range of five to eight millimeters in diameter, although they may be larger (e.g., 14 mm) or smaller (e.g., 3 mm). The diminutive scale of the mechanisms in the surgical instrument 120 creates unique mechanical conditions and issues with the construction of these mechanisms that are unlike those found in similar mechanisms constructed at a larger scale, because forces and strengths of materials do not scale at the same rate as the size of the mechanisms. The drive elements must fit within the elongate tube 210.

FIGS. 3 through 6 are views of an exemplary surgical end effector 260 that may be used with the invention. End effector 260 illustrates various distal components with one or more rotating or translating parts that can be controlled in accordance with inventive aspects, such as stapler components, knife blades, jaws and arms, mechanical camera control, etc.

Figure 3:
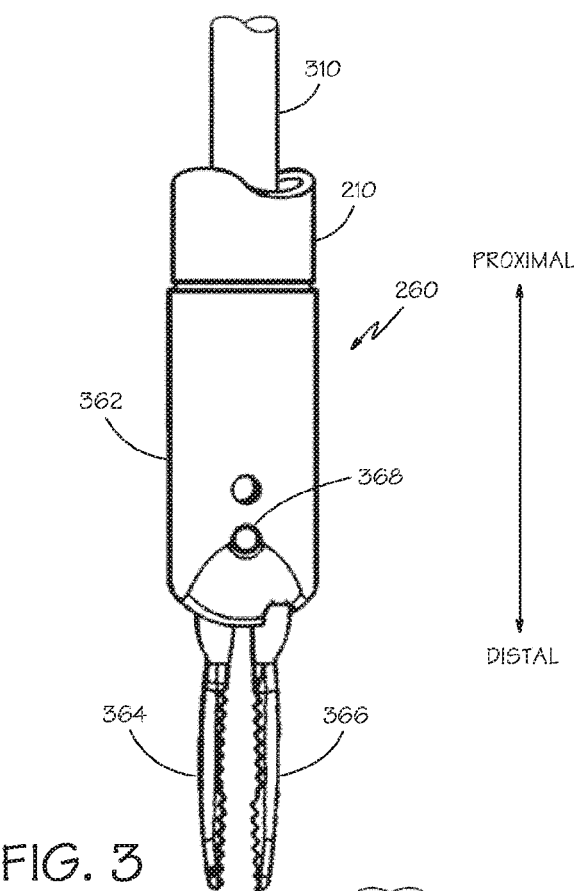
FIG. 3 is a front elevation of an exemplary surgical end effector.
Figure 4:
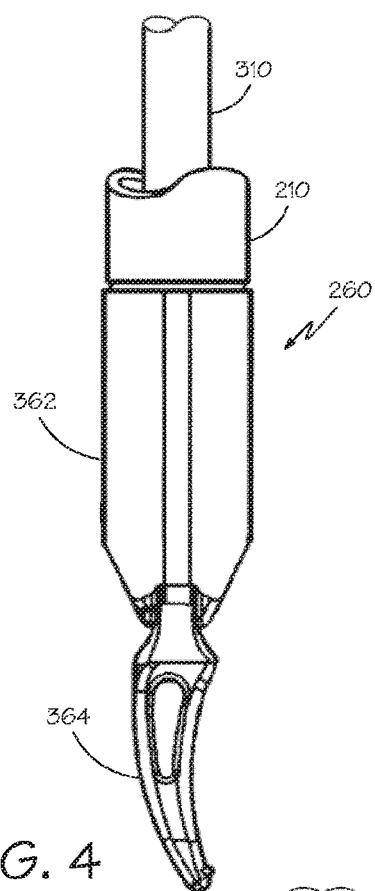
FIG. 4 is a side elevation of the exemplary surgical end effector.

FIG. 3 is a front elevation, and FIG. 4 is a side elevation, of the exemplary surgical end effector 260. A clevis 362 is fixed to the distal end of the elongate tube 210, either directly (as shown) or by a wrist mechanism (not shown) that allows the end effector's longitudinal axis to rotate with reference to the tube's longitudinal axis. The clevis 362 supports two jaws 364, 366 that are coupled to the clevis by a pivot pin 368. The two jaws 364, 366 can rotate about the pivot pin 368 to open and close the two jaws against one another. In this example, rotation of the elongate tube 210 causes the clevis 362 and the two jaws 364, 366 to rotate in unison with the elongate tube, thus reorienting the end effector in roll with reference to the proximal control mechanism 240. In other embodiments, the end effector optionally may be fixed or may roll with reference to the tube.

Figure 5:
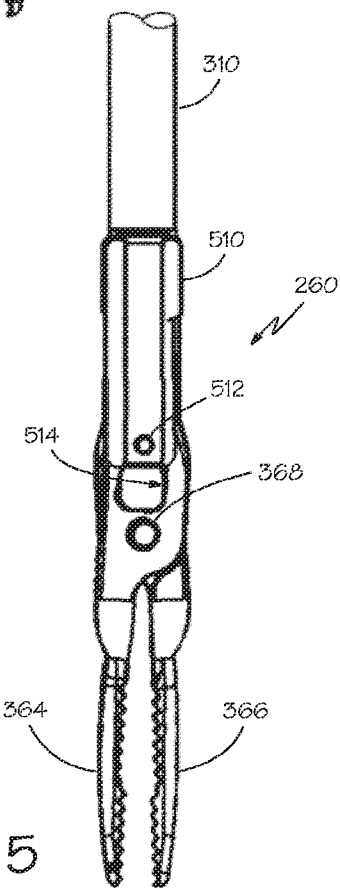
FIG. 5 is a front elevation of an exemplary surgical end effector with parts removed.
Figure 6:
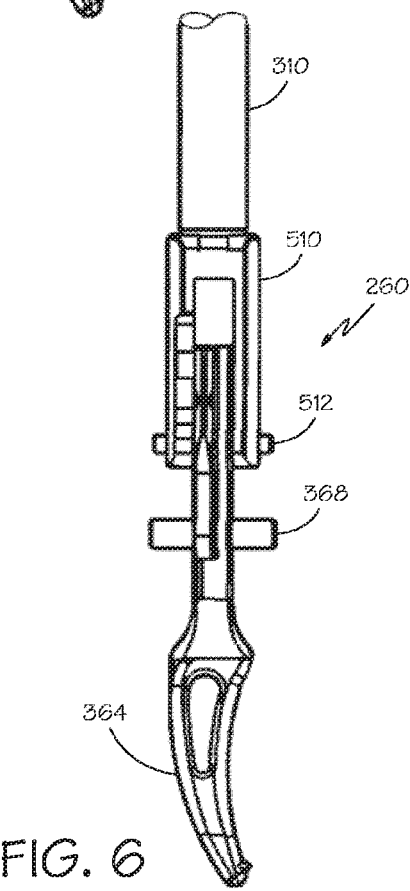
FIG. 6 is a side elevation of the exemplary surgical end effector with parts removed.

FIG. 5 is a front elevation, and FIG. 6 is a side elevation, of the exemplary surgical end effector 260 with the elongate tube 210 and the clevis 362 removed so the arrangement of the two jaws 364, 366 can be seen. A yoke 510 is fixed to the distal end of a drive element 310 that extends from the proximal control mechanism 240 through tube 210. A drive pin 512 is supported by the yoke 510. Each of the two jaws 364, 366 include a cam slot 514, and drive pin 512 extends through cam slots 514. The two jaws open and close as the drive element 310 is pushed in a distal direction and pulled in a proximal direction to cause drive pin 512 to bear against the walls of cam slots 514.

It will be appreciated that the present invention can be used with any surgical end effector that is actuated by a push-pull drive element. The cam pin and cam slots illustrate one of many ways the movement of one or more moving parts of a distal end component of the instrument may be controlled by translation of drive element 310, including cam surfaces, levers, short flexible elements, and the like.

FIGS. 7 through 10 are schematics of a force transmission that incorporates inventive aspects. For clarity, some hidden edges are shown with dashed lines, while other hidden edges are not shown.

Figure 7:
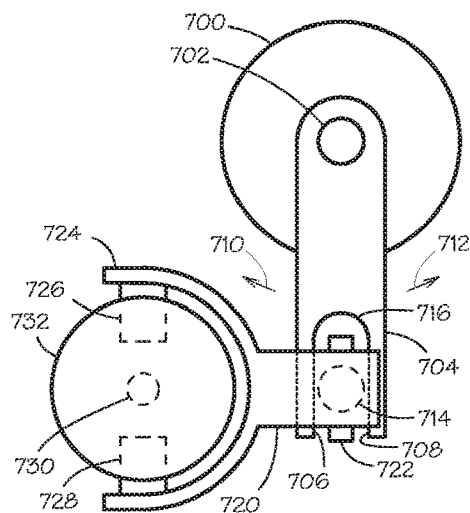
FIG. 7 is a top view of a schematic representation of an embodiment of a force transmission used to control an end effector of a surgical instrument.

FIG. 7 shows the proximal end of a surgical instrument that includes the force transmission, with a line of sight along the longitudinal axis of the drive element 730 (i.e., drive element 730 moves in and out of the page as shown). For the purposes of this description, this will be referred to as the top view. Some components of the force transmission are supported by a chassis that is not shown for clarity. The chassis serves as a mechanical ground and provides a frame of reference for the force transmission mechanism and its components. Connection of components to the chassis is as described.

An actuator 700, such as an electrical motor, rotates a shaft 702 in response to commands from a user of the surgical system in which the force transmission is deployed. For example, a surgeon may operate one or more controls on a user control station to indirectly manipulate the instrument that is connected to the force transmission by controlling the actuator 700 to rotate the shaft 702. The movement of controls on the console are translated into signals to control one or more actuators by a computer control system that allows control motions to be used on the console without regard to the actuator motions required to respond to the control motions. The actuator 700 is optionally part if the instrument or in a manipulator to which the instrument is coupled, as described above. If in a manipulator separate from the instrument, an interface between actuator 700 and shaft 702 is provided so that the actuator output is easily coupled to and uncoupled from the shaft 702. In a da Vinci® Surgical System implementation, for example, a rotating drive output is engaged with a rotating drive input coupled to the shaft.

An arm 704 is attached to the shaft 702 such that the arm is rotated when the actuator 700 rotates the shaft. The arm 704 and shaft 702 are supported by the chassis such that the only degree of freedom with respect to the chassis is the rotation around the axis of rotation of the shaft 702. A slot 716 having two side walls 706, 708 is at the end of the arm 704 opposite the end of the arm that is coupled to the shaft 702. Persons of skill in the art will understand that arm 704 represents a lever with a fulcrum at shaft 702's axis of rotation and a resistance point at slot 716, and so other ways of applying the necessary effort to rotate arm 704 may optionally be used instead of shaft 702 (e.g., connecting rods, cams, and the like).

A lever 720 supported by the chassis on a pivot 722 that provides the fulcrum for the lever. The lever 720 may be in the form of a bell crank, in which the two arms of the lever meet at a non-zero angle to one another at the pivot 722. In the example shown in FIGS. 7-10, the arms of the lever 720 meet at a ninety-degree (right) angle at the pivot 722, although the angle may be less (acute) or more (obtuse). The lengths of the two arms of the lever 720 may be unequal to provide a mechanical advantage and/or change the range of motion of the lever's resistance point.

A ball 714 is fixed to one end of the lever 720. A fork 724 is formed on the other end of the lever 720. The ball 714 is received in the slot 716 formed in the end of the arm 704. Rotation of the arm 704, as suggested by the arrows 710, 712, applies a force to the ball 714 on the end of the lever 720. Ball 714 illustrates various protrusions at the end of lever 720 that may be received in slot 716, and other protrusion shapes suitable to be received in the slot 716 may be used.

Figure 8:
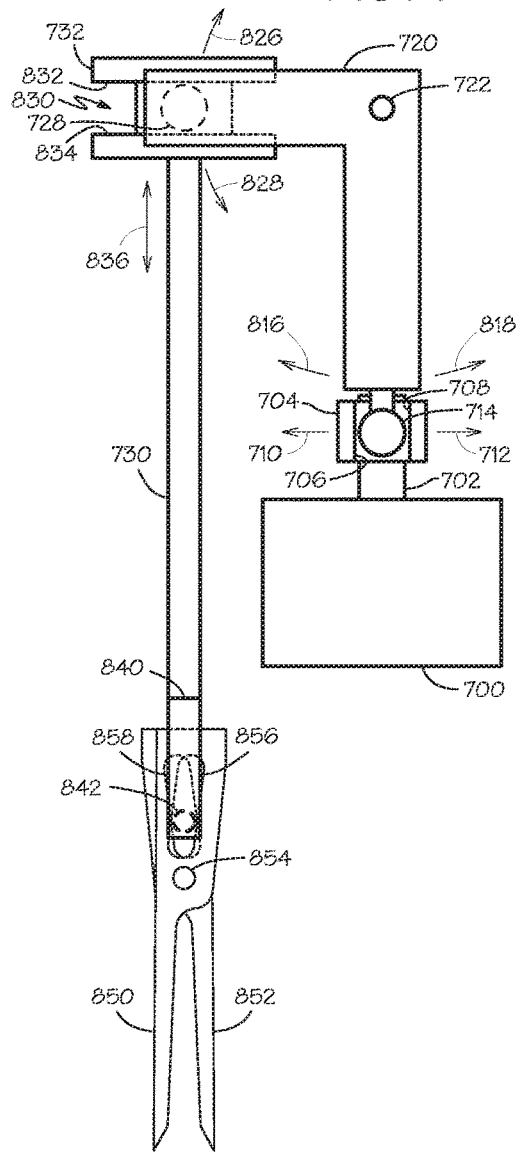
FIG. 8 is a front view of the force transmission shown schematically in FIG. 7.

FIG. 8 shows the proximal end of the force transmission with a line of sight along the longitudinal axis of the pivot 722 (i.e., the axis of rotation at pivot 722 for the lever 720 extends out of the page). For the purposes of this description, this will be referred to as the front view.

As seen in the front view of FIG. 8, rotation of the arm 704 causes one of the two side walls 706, 708 of the slot 716 in the arm to apply a force to the ball 714 on the end of the lever 720. This causes the lever 720 to rotate about the longitudinal axis of the pivot 722, as suggested by the arrows 816, 818. The opposite end of the lever 720 therefore rotates, as suggested by the arrows 826, 828. As arm 704 rotates, ball 714 translates a small distance within slot 716.

The opposite end of the lever 720 includes the fork 724, which supports two inwardly facing pins 726, 728. Pins 726, 728 are shown as circular cylinders, although other suitable pin shapes (e.g., oval) may be used. And, a single pin may be used. The cylindrical pins 726, 728 are received in an annular recess 830 in a proximal termination 732 of the drive element 730. The cylindrical pins 726, 728 have a common longitudinal axis that lies in a plane that is perpendicular to the longitudinal axis of the drive element 730 and is parallel to the axis of rotation of pivot 722. The drive element 730 and the attached proximal termination 732 are free to rotate about the longitudinal axis of the drive element because the pins travel within annular recess 830 as drive element 730 rotates.

A surgical end effector, such as the pair of jaws 850, 852 shown, is supported at the distal end of an elongate tube (not shown). The surgical end effector may be a pair of jaws pivotally supported by a clevis fixed to an end of an elongate tube as shown in FIGS. 3-6. The surgical end effector is actuated by the drive element 730. For example, the distal end of the drive element 730 may be coupled to a yoke 840 that supports a drive cam pin 842 to move within cam slots 856, 858 on the jaws 850, 852 and cause the jaws to open and close, as described above.

The elongate tube (not shown) is supported at its proximal end by the chassis. The elongate tube in turn supports the surgical end effector at the distal end of the elongate tube. The elongate tube may be supported by the chassis such that the elongate tube can rotate about its longitudinal axis. The drive element 730 may be keyed to the elongate tube such that the drive element rotates in unison with the elongate tube while remaining free to translate along the length of the elongate tube to actuate the surgical end effector jaws 850, 852, as suggested by the two-headed arrow 836.

When the arm 704 rotates and causes the lever 720 to rotate, the fork 724 and the two inwardly facing cylindrical pins 726, 728 move as suggested by the arrows 816, 818. This pin movement applies a force to one of the two opposing surfaces of the annular recess 830 in the proximal termination 732 of the drive element 730, and so translates the drive element along the length of the elongate tube to actuate the surgical end effector 850, 852, as suggested by the two-headed arrow 836. As lever 720 rotates, the pins 724, 728 also translate a small distance in the same direction, and annular recess 830 accommodates this small common translation. If the common translation (i.e., lever 720's rotational range of motion) is sufficiently small, no significant change in leverage occurs. Likewise, translation of the ball 714 in slot 716 of arm 704.

Figure 9:
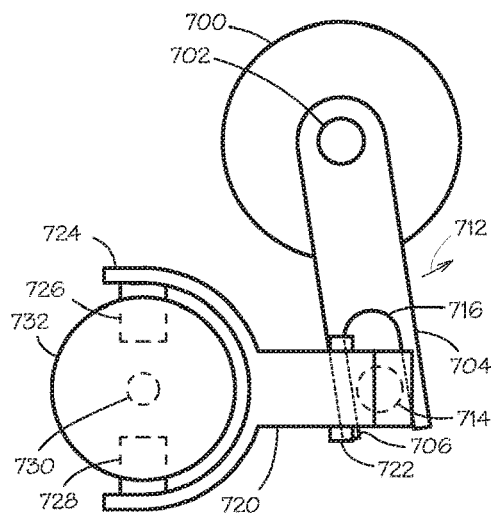
FIG. 9 is a top view of the force transmission shown schematically in FIG. 7 in another operative position.
Figure 10:
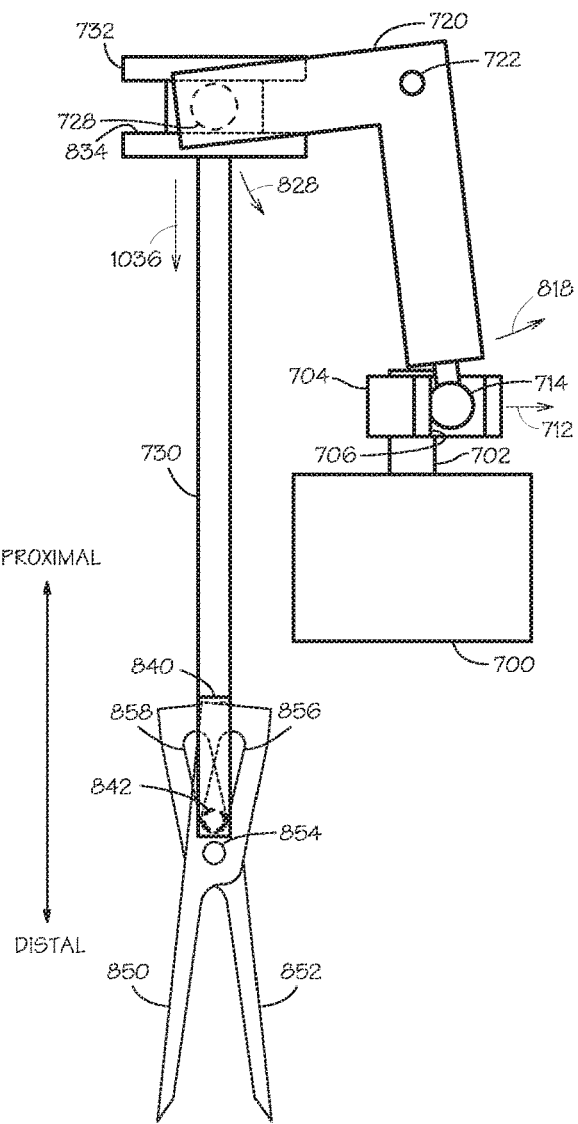
FIG. 10 is a front view of the force transmission shown schematically in FIG. 9.

FIGS. 9 and 10 show the force transmission with the arm 704 having been rotated by the actuator 700 in a counter-clockwise direction as viewed from the top and as suggested by the arrow 712. The rotation of the arm 704 causes one wall 706 of the slot 716 apply a force to the ball 714 on one end of the lever 720, thus rotating the lever as suggested by the arrows 818, 828. The rotation of the lever 720 causes the two inwardly facing cylindrical pins 726, 728 to apply a force to the lower surface 834 of the annular recess 830 in the proximal termination 732 of the drive element 730. The force applied to the proximal termination 732 causes the drive element 730 to move distally toward the surgical end effector 850, 852 and, for the example surgical end effector shown, causes the jaws to open.

It will be appreciated that other surgical end effectors that are actuated by a drive element can be used with the invention. Other surgical end effectors may provide different motions other than opening and closing of two jaws when actuated by a drive element. For example, the drive element may actuate a stapler, a clip applier, a knife blade, or the like. Couplings other than a yoke, drive pin, and slots may be used to transfer the actuation forces of the drive element to the surgical end effector's one or more moving parts. For example, the drive element may actuate the moving parts directly, by a rack and pinion connection, by various forms of linkages, or the like.

FIGS. 11 through 17 show another force transmission that incorporates inventive aspects. The structure and function of this force transmission is similar to that of the force transmission described above unless otherwise described below.

Figure 11:
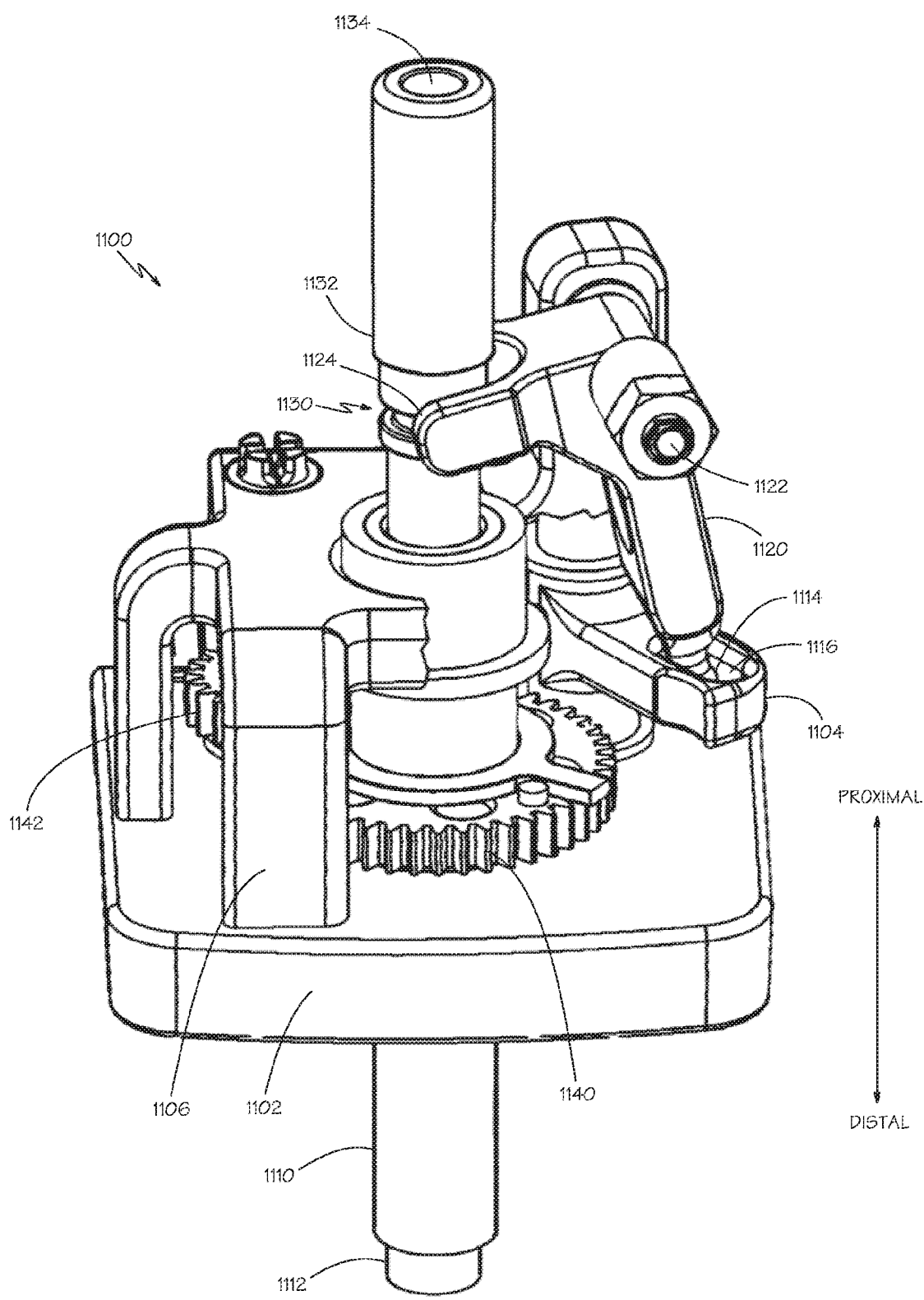
FIG. 11 is a pictorial view of another force transmission.

FIG. 11 is a pictorial view of the proximal end of a surgical instrument 1100 that includes the force transmission. A chassis 1102 with an attached frame 1106 supports some components of the force transmission and serves as a mechanical ground and frame of reference for the force transmission mechanism. A portion of the attached frame 1106 has been cut away to allow components of the force transmission to be seen.

An actuator (not shown), such as an electrical motor, is coupled to the proximal end of surgical instrument 1100 to actuate a distal surgical end effector in response to commands from a user of the surgical system in which the surgical instrument is deployed, as described above. For example, a surgeon can operate one or more controls on a user control unit to indirectly manipulate the surgical end effector that is connected to the force transmission by controlling the actuator to rotate arm 1104. The movement of the one or more controls on the user control unit are translated into signals to control one or more actuators by a computer control system that allows control motions to be used on the console without regard to the actuator motions required to respond to the control motions. The actuator may be arranged to be easily coupled to and uncoupled from the arm 1104, as described above.

The arm 1104 is supported by the chassis such that the only degree of freedom with respect to the chassis is the rotation around the axis of rotation of the rotational actuator input coupled to the arm by a shaft, as described above. A slot 1116 having two side walls is at the end of the arm 1104 opposite the end of the arm that is coupled to the actuator.

A lever 1120 supported by the chassis on a pivot 1122 that provides the fulcrum for the lever. As shown, lever 1120 is a bell crank, as described above.

A ball 1114 is fixed to one end (the effort end) of the lever 1120. The ball 1114 is received in the slot 1116 at the end of the arm 1104. Rotation of the arm 1104 applies a force to the ball 1114 on the end of the lever 1120.

The opposite end (the resistance end) of the lever 1120 includes a fork 1124. The fork engages a proximal termination 1132 of the drive element 1112. An elongate tube 1110 is supported at its proximal end by the chassis 1102. The drive element 1112 passes through the interior passage of the elongate tube 1110. As shown, the drive element 1112 optionally may be a tube that provides a fluid passage from a fluid port 1134 at the proximal end of the drive element to the distal end effector 260. A flexible tube (not shown) may be coupled between fluid port 1134 and a fluid input port to the instrument, and the tube is arranged (slack loop, coil, etc.) to accommodate drive element 1112 rotation. Alternatively, fluid port 1134 is directly accessible on the instrument.

FIGS. 12 through 15 are top views of the proximal end of the surgical instrument with a line of sight along the axis of rotation for the arm 1104. Various components are hidden to allow other components to be clearly seen in these Figures.

Figure 12:
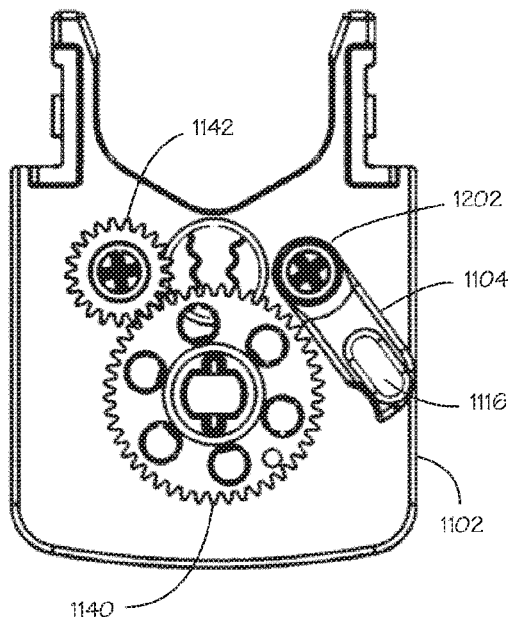
FIG. 12 is a plan view of the force transmission shown in FIG. 11 with various components removed.
Figure 13:
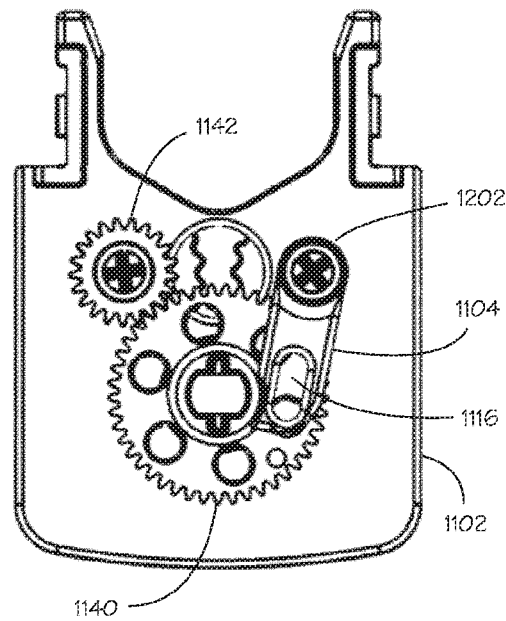
FIG. 13 is a plan view of the force transmission shown in FIG. 12 in another operative position.

FIG. 12 shows the arm 1104 in a position that represents a first end of the arm's range of motion because of interference between the arm and a cover (not shown) for the proximal mechanism of the surgical instrument. FIG. 13 shows the arm 1104 in another position that represents a second end of the arm's range of motion because of interference between the arm and the proximal termination 1132 of the drive element 1112.

Figure 14:
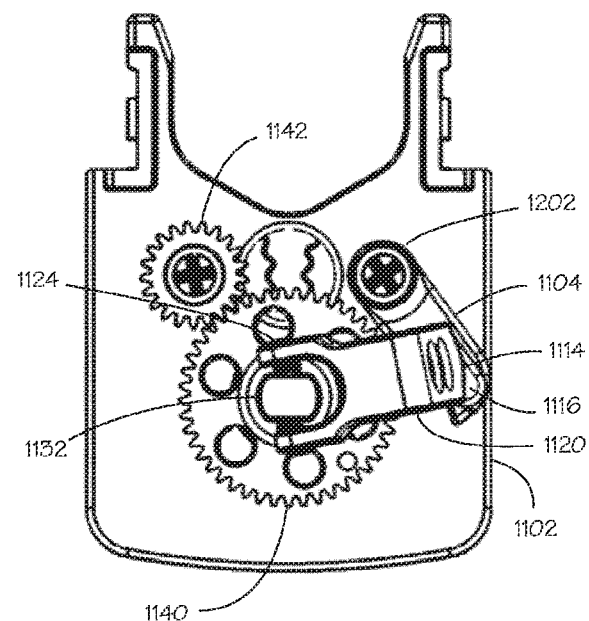
FIG. 14 is a plan view of the force transmission shown in FIG. 12 with additional components shown.
Figure 15:
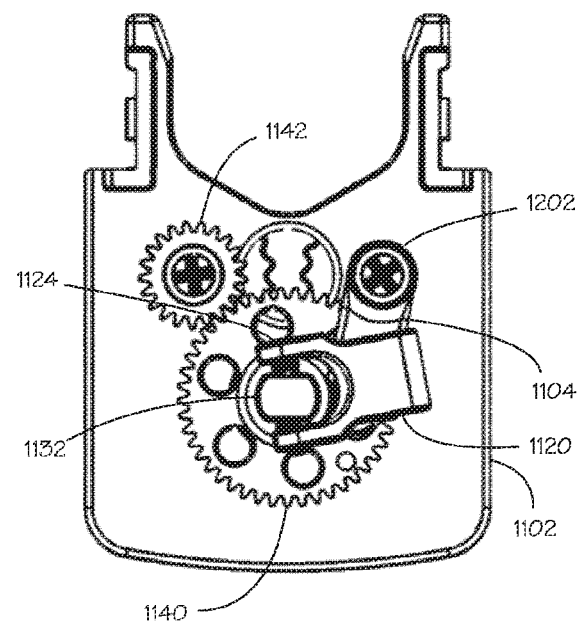
FIG. 15 is a plan view of the force transmission shown in FIG. 13 with additional components shown.

FIG. 14 shows the lever 1120 with the ball 1114 in the slot 1116 of the arm 1104 at the first end of arm 1104's range of motion. FIG. 15 shows the lever 1120 with the ball (not visible) in the slot (not visible) of arm 1104 at the second end of arm 1104's range of motion.

Figure 16:
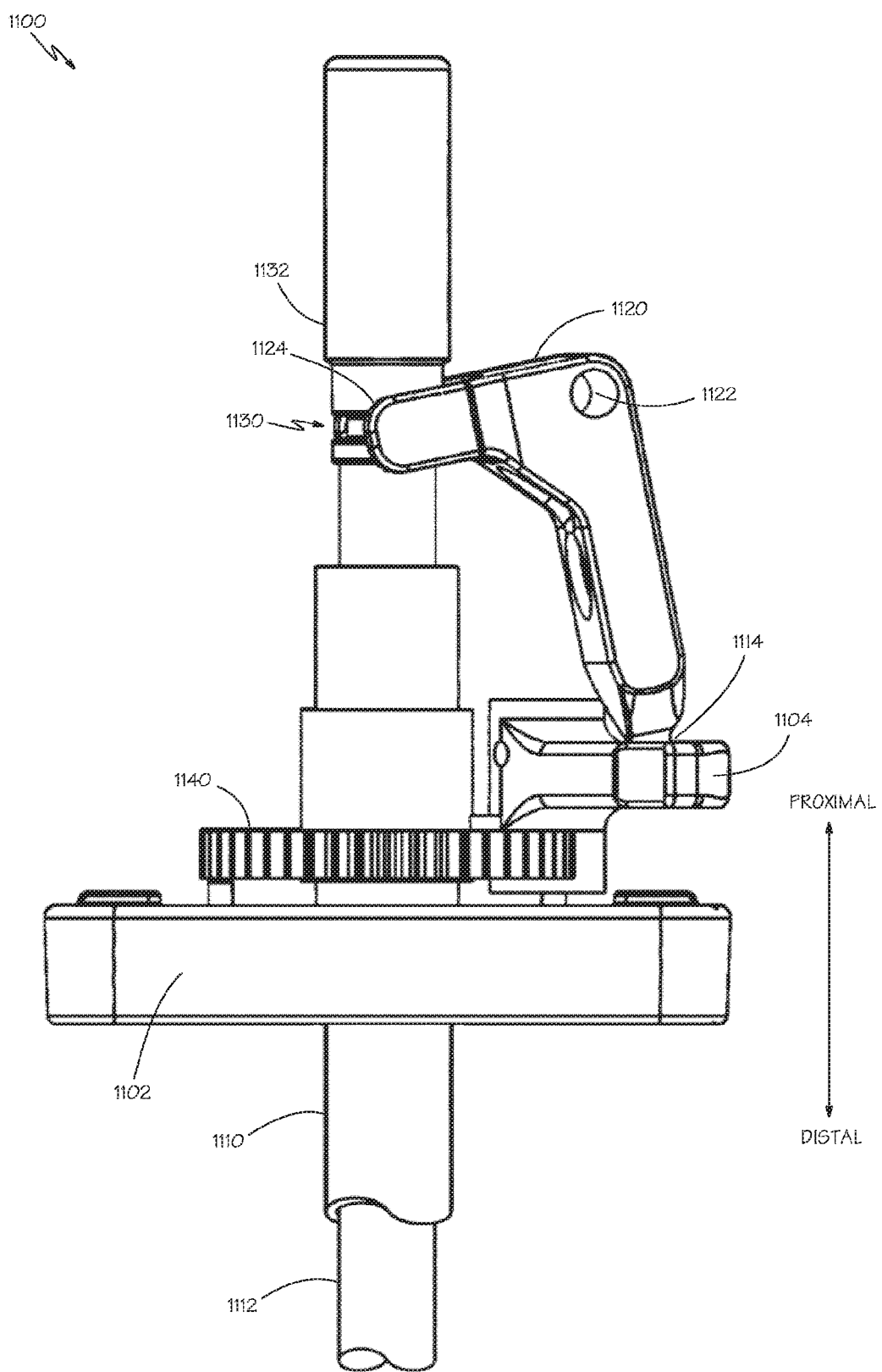
FIG. 16 is a front view of the force transmission shown in FIG. 14.
Figure 17:
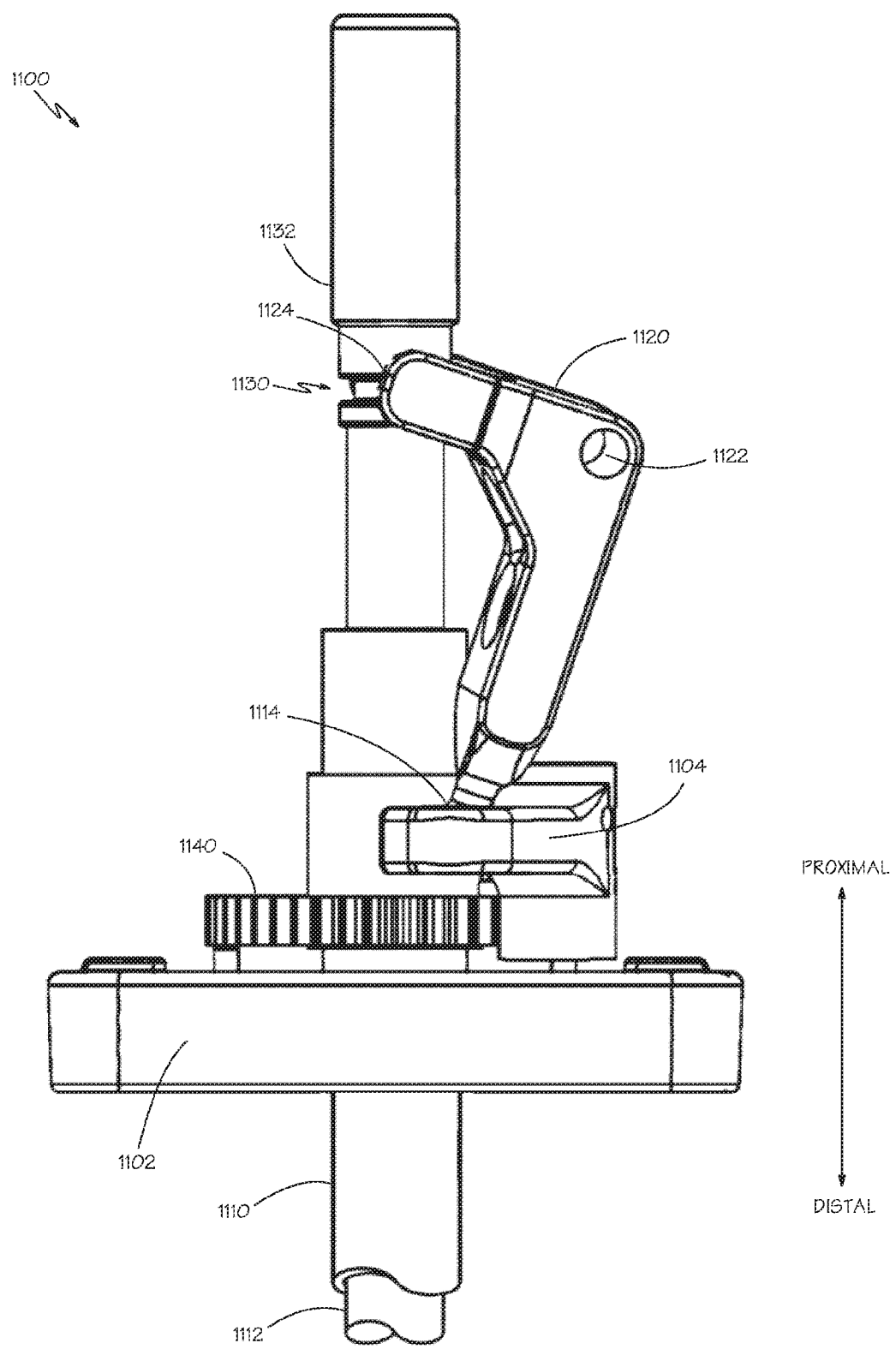
FIG. 17 is a front view of the force transmission shown in FIG. 15.

FIGS. 16 and 17 are front views of the proximal end of the surgical instrument with a line of sight perpendicular to the axis of rotation for the arm 1104. Various components are hidden to allow other components to be clearly seen in these Figures.

FIG. 16 shows the lever 1120 with the ball 1114 in the slot (not visible) of the arm 1104 at the first end of arm 1104's range of motion. FIG. 17 shows the lever 1120 with the ball (not visible) in the slot (not visible) of the arm 1104 at the second end of arm 1104's range of motion. It will be seen that the rotation of the arm 1104 is translated into a linear motion of the drive element 1112. As shown, arm 1104's range of motion is sufficient to cause the desired range of motion for drive element 1132.

The fork 1124 on one end of the lever 1120 supports two inwardly facing pins (not visible) as described above. The cylindrical pins engage an annular recess 1130 in the proximal termination 1132 of the drive element 1112. The cylindrical pins have a common longitudinal axis that lies in a plane that is perpendicular to the longitudinal axis of the drive element 1113. The drive element 1113 and the attached proximal termination 1132 are free to rotate about the longitudinal axis of the drive element as the cylindrical pins slide within the annular recess 1130.

The elongate tube 1110 is supported at its proximal end by the chassis. The elongate tube may be supported by the chassis such that the elongate tube can rotate about its longitudinal axis. The drive element 1112 may be keyed to the elongate tube 1110 such that the drive element rotates in unison with the elongate tube while remaining free to move along the length of the elongate tube to actuate a surgical end effector.

The surgical instrument may include, or provide a mechanism for coupling, a second teleoperated actuator, such as an electric motor, to rotate the elongate tube 1110 and the drive element 1112, and thereby rotate a surgical end effector (not shown) that is supported at a distal end of the elongate tube. In the embodiment shown, a first gear 1140 (FIG. 12) is coupled to the elongate tube 1110, and a second gear 1142 engages the first gear. Rotation of the second gear 1142 by the second actuator causes the elongate tube 1110 and the drive element 1112 to rotate. The coupling between the lever 1120 and the proximal termination 1132 of the drive element 1112 allows the proximal termination to be rotated by the second actuator without affecting the transmission of forces from the lever 1120 to the drive element from the first actuator, which rotates the arm 1104.

Figure 18:
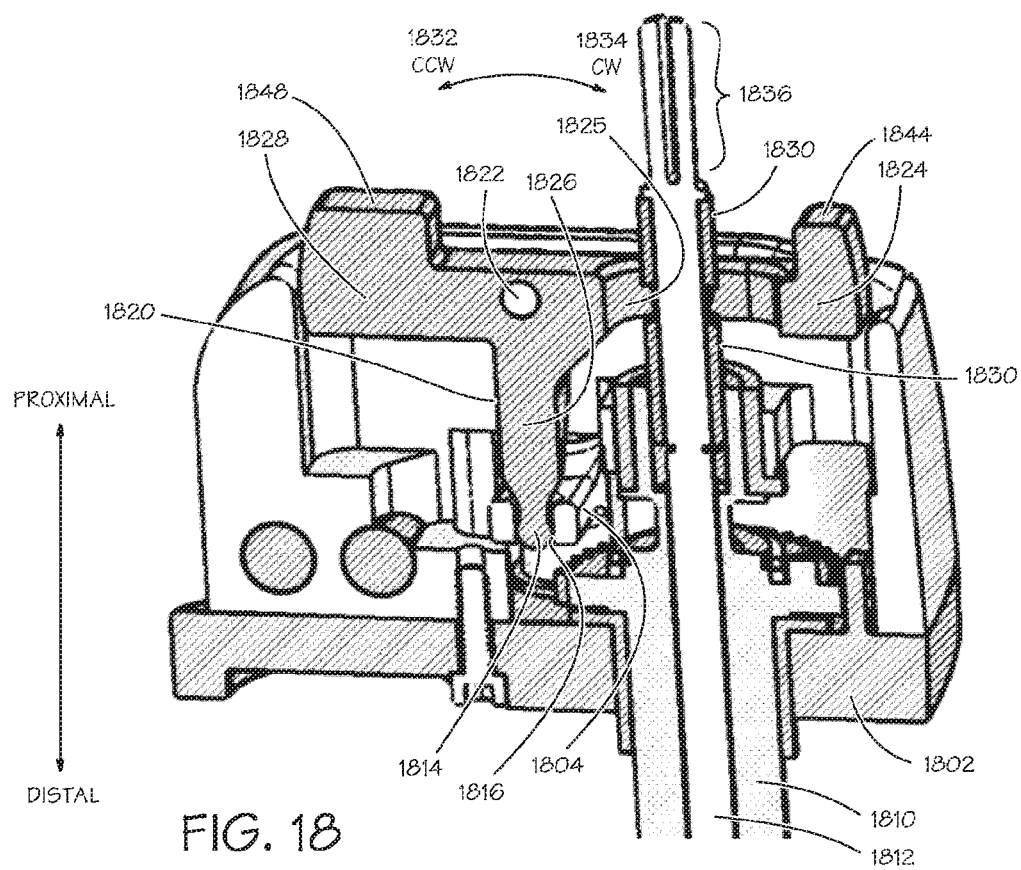
FIG. 18 is a perspective view that shows a cross section of another force transmission mechanism.

FIG. 18 shows a cross-section of another force transmission mechanism that embodies the invention. The structure and function of this force transmission is similar to that of the force transmissions described above unless otherwise described below. The force transmission mechanism includes a chassis 1802 that supports a central drive element 1812 that passes through a central interior passage of an elongate tube 1810. (Only the proximal portion of the elongate tube 1810 is shown.) During operation, the elongate tube 1810 can rotate relative to the chassis 1802, and the central drive element 1812 can translate axially relative to the elongate tube 1810. Translation of the central drive element 1812 actuates an end effector. For example, translation of the central drive element 1812 may open and close jaws 364, 366 of a gripper element for the end effector portion 260.

During operation, rotary drive inputs of the proximal control mechanism engage with motor outputs (not shown) of a robotic manipulator assembly of a teleoperated surgical system. One rotary drive input is coupled to a rotational arm 1804. The rotational arm 1804 includes a slot 1816 that engages a lever 1820. As shown, lever 1820 is configured as a rocker by extending one of the two arms. The lever 1820 pivots relative to the chassis 1802 about a pivot pin 1822. The lever 1820 is a bell crank type lever with the arms 1824, 1826 extending from the pivot 1822 at an angle to one another, such as a right angle as shown. The lever 1820 includes a ball feature 1814. The slot 1816 of the rotational arm 1804 engages with the ball feature 1814 of the lever 1820. When the rotary drive input is rotated, this rotational motion is transferred to the rotational arm 1804, which in turn rotates the lever 1820 about the pivot pin 1822.

The lever 1820 includes a slot 1825, and a collar feature 1830 is fixed to the central drive element 1812 such that collar and drive element rotate and translate in unison. Collar feature 830 includes an annular recess, and the sidewalls of slot 1825 are engaged in the annular recess so that collar feature can roll within slot 1825 and translate as lever 1820 rotates. The edges of slot 1825 and of collar feature 830's annular recess are shaped to minimize backlash for collar feature 1830's translations while accommodating the small rotations of slot 1825's sidewalls with reference to collar feature 1830 as lever 1820 rotates.

As shown, when the end of the lever 1820 rotates in a counter-clockwise direction 1832 as seen in the figure, the central drive element 1812 is moved in a proximal direction by the force of the slotted lever arm 1824 acting on the collar feature 1830. When the lever 1820 pivots in a clockwise direction 1834, the central drive element 1812 moves in a distal direction by the force of the slotted lever arm 1824 acting on the opposite side of the collar feature 1830. The central drive element 1812 and the collar feature 1830 are free to rotate relative to lever 1820 and slot 1825.

In one embodiment, the central drive element 1812 is made from an electrically conductive material. A proximal end of the central drive element 1812 extends beyond the proximal control mechanism to include a electrical connector 1836 (illustrated by a pin, as shown). An electrical cable connected to an output of an electrosurgical energy generator (e.g., an electrocautery generator) (not shown) can be removably attached to the connector pin 1836 to deliver electrosurgical energy (e.g., monopolar cautery energy) to the central drive element 1812. In one aspect, the central drive element 1812 is electrically coupled to the end effector portion 260 by making the components that mechanically couple the central drive element 1812 to the end effector portion 260 from electrically conductive materials. When the end effector portion 260 is coupled to the central drive element 1812, electrosurgical energy can be delivered to the end effector 260, such as to a gripper element located at the distal end of the elongate tube 1810. This electrically conductive drive element feature and connector may be incorporated into other embodiments described herein.

Figure 19:
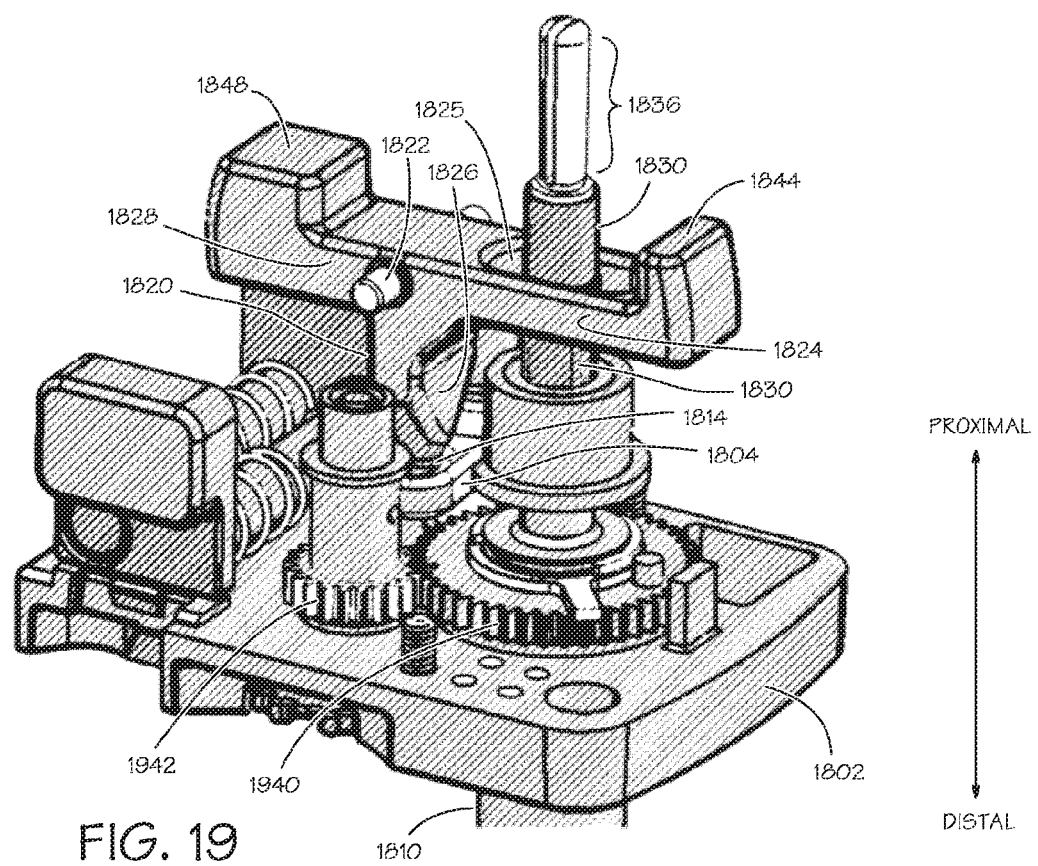
FIG. 19 is a perspective view of the force transmission mechanism shown in FIG. 18.

FIG. 19 shows a perspective view of the force transmission mechanism shown in FIG. 18. The elongate tube 1810 extends through and rotates relative to the chassis 1802. A driven tube roll gear 1940 is rotationally keyed to the elongate tube 1810. A second rotary drive input is rotationally coupled to an input gear 1942 that engages the tube roll gear 1940. When the second rotary drive input rotates, it rotates the tube roll gear 1942. During operation, rotation of the second rotary drive input rotates the input gear 1942, which in turn rotates the tube roll gear 1940 and the elongate tube 1810.

Figure 20A:
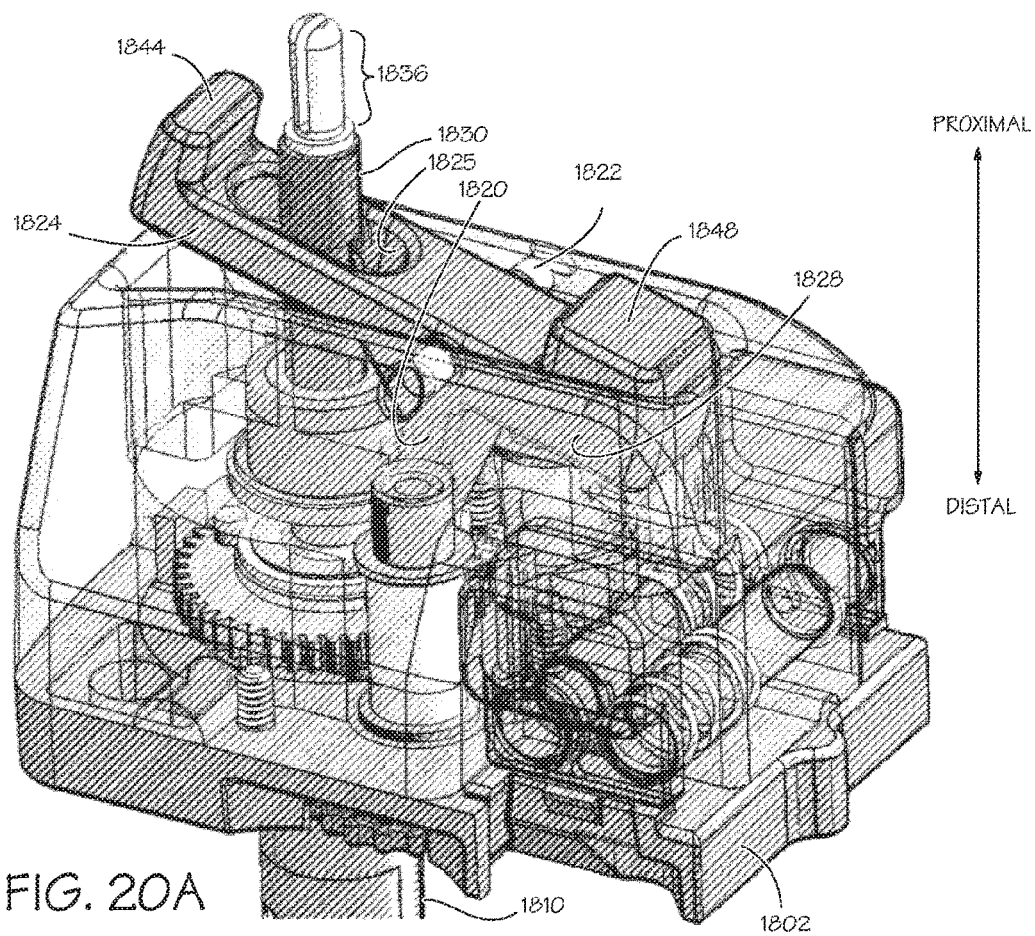
FIG. 20A is a perspective view of the force transmission mechanism shown in FIG. 18 with a cover in place.
Figure 20B:
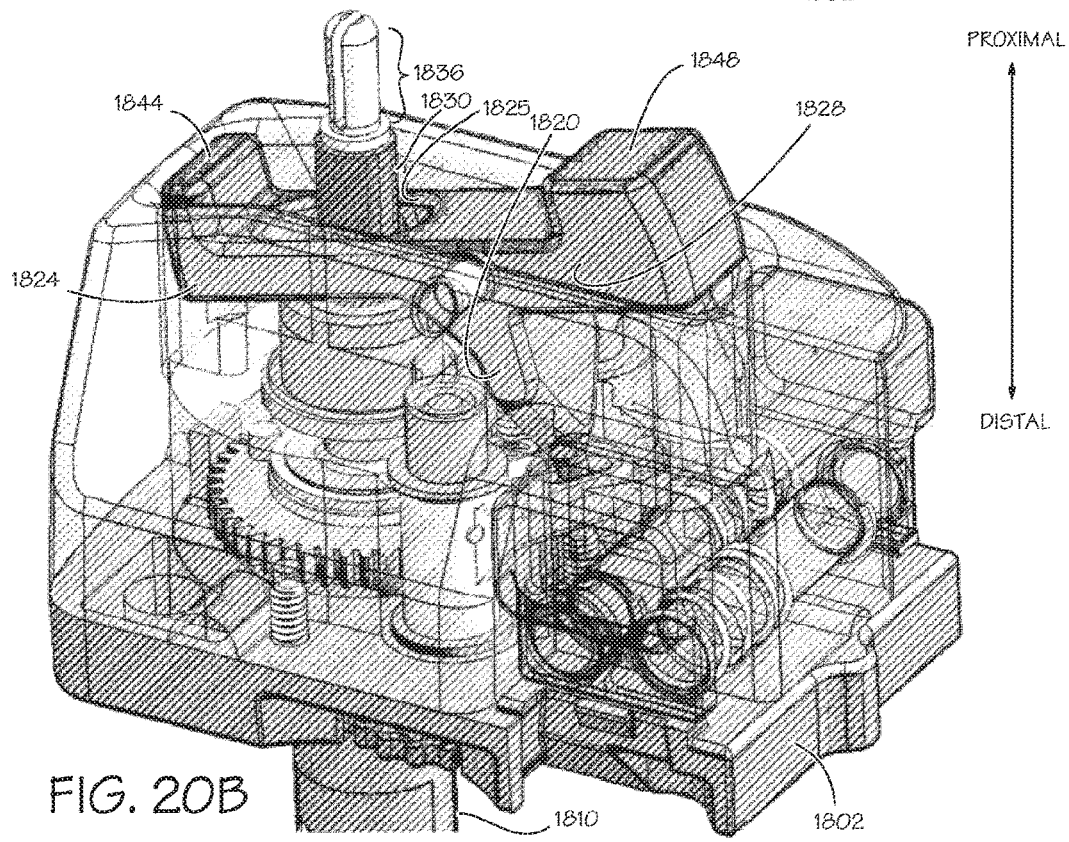
FIG. 20B is the force transmission mechanism shown in FIG. 20A in an alternate operative position.

FIG. 20A and FIG. 20A show perspective views of the force transmission mechanism shown in FIG. 18 with a cover 2000 over the force transmission mechanism. The cover 2000 is shown with transparency so the elements of the force transmission mechanism can be seen. The lever 1820 includes a third arm 1828 that extends from the pivot 1822 on the opposite side from the slotted arm 1824. While the third arm 1828 and the slotted arm 1824 are shown extending along a straight line, in some embodiments these arms may be at other angles with respect to one another. It will be appreciated that the third arm 1828 and the slotted arm 1824 provide another lever in a rocker configuration (class 1 lever) that can rotate the arm 1820 and so translate the central drive element 1812.

Proximally extending protrusions 1844 may be provided at the end of slotted arm 1824, and protrusion 1848 may be provided at the end of third arm 1828. The protrusions 1844, 1848 extend from the ends of the slotted arm 1824 and third arm 1828 beyond the cover 2000. The protrusions provide a means for manually operating the end effector, particularly when the proximal control mechanism is not coupled to a robotic manipulator assembly of a teleoperated surgical system. The protrusions also provide a visual indication of the operative position of the end effector 260. This rocker configuration feature may be combined with other embodiments described herein when the geometries are suitably modified.

While certain exemplary embodiments have been described and shown in the accompanying drawings, it is to be understood that such embodiments are merely illustrative of and not restrictive on the broad invention, and that this invention is not limited to the specific constructions and arrangements shown and described, since various other modifications may occur to those of ordinary skill in the art. The description is thus to be regarded as illustrative instead of limiting.

What is claimed is:
1. A force transmission mechanism comprising:
   a chassis;
   a shaft rotatably mounted in the chassis, the shaft being rotatable about a first axis;
   an arm comprising a first end portion and a second end portion opposite the first end portion, the arm having a length extending laterally from the shaft from the first end portion to the second end portion, the arm being rotatable about the first axis, and the arm including a slot having a length extending between the first end portion and the second end portion;

a lever supported by the chassis, the lever being free to rotate relative to the chassis, the lever having a first end, a second end opposite the first end, and a protrusion at the first end of the lever, and the protrusion being translatable along the length of the slot; and a drive element supported by the chassis, the drive element being free to translate relative to the chassis along a second axis, the second axis being parallel with the first axis, the drive element including a first end and a proximal termination at the first end of the drive element, and the proximal termination being engaged with the second end of the lever.

2. The force transmission mechanism of claim 1, wherein the drive element comprises a fluid channel between proximal and distal ends of the drive element.

3. The force transmission mechanism of claim 1, wherein the drive element comprises an electrically conductive path between proximal and distal ends of the drive element.

4. The force transmission mechanism of claim 1, wherein:
the shaft comprises an elongate tube having a first end supported by the chassis and a second end opposite the first end;
an end effector is coupled to the second end of the elongate tube;
the drive element extends from the proximal termination through the elongate tube to the end effector; and
the drive element is configured to translate along the second axis relative to the elongate tube to actuate the end effector.

5. The force transmission mechanism of claim 4, wherein the elongate tube is free to rotate relative to the chassis, the drive element is constrained to rotate in unison with the elongate tube, and the proximal termination of the drive element is free to rotate relative to the second end of the lever.

6. The force transmission mechanism of claim 5, wherein:
an annular recess is defined in the proximal termination;
the second end of the lever further comprises a fork;
the fork comprises a first fork arm and a second fork arm; and
the first fork arm and the second fork arm are configured to engage with the annular recess.

7. The force transmission mechanism of claim 6, wherein the first fork arm and the second fork arm comprise at least one pin engaged with the annular recess.

8. The force transmission mechanism of claim 4, wherein the drive element comprises a drive element tube that comprises a fluid passage extending from the proximal termination to the end effector.

9. The force transmission mechanism of claim 1, wherein:
the lever comprises a first lever arm, a second lever arm, and a third lever arm;
the first lever arm extends between a pivot of the lever and the first end of the lever;
the second lever arm extends between the pivot of the lever and the second end of the lever; and
the third lever arm extends from the pivot of the lever opposite the second lever arm.

10. The force transmission mechanism of claim 1, wherein a first lever arm and a second lever arm of the lever intersect at a ninety-degree angle at a pivot that supports the lever on the chassis.

11. The force transmission mechanism of claim 1, wherein:
a lever slot is located in the second end of the lever, and the drive element comprises a collar engaged with the slot of the lever.

12. The force transmission mechanism of claim 1, wherein the protrusion at the first end of the lever comprises a ball received by the slot.

13. The force transmission mechanism of claim 1, wherein the length of the slot extends perpendicularly relative to the first axis.

14. A method for transmitting a force, the method comprising:
rotating an arm supported by a chassis about a first axis, the arm including a slot having a length, and the length of the slot extending perpendicularly from the first axis;
rotating a lever supported by the chassis, the lever having a first end, a second end opposite the first end, and a protrusion at the first end of the lever, the protrusion being translatable along the length of the slot, the lever being rotated by the rotation of the arm; and
translating a drive element supported by the chassis along a second axis, the second axis being parallel with the first axis, the drive element having a proximal termination that engages the second end of the lever, the drive element being pushed by the rotation of the lever.

15. The method for transmitting forces of claim 14, further comprising:
actuating an end effector fixed to an elongate tube with the drive element being pushed through the elongate tube to transfer a pushing force applied at the first end of the drive element to the end effector.

16. A force transmission mechanism comprising:
a chassis;
a shaft supported by the chassis, the shaft being rotatable about a first axis;
an arm coupled to and rotatable with the shaft, the arm having a length extending perpendicularly from the shaft, and the arm being rotatable about the first axis;
a lever supported by the chassis, the lever being free to rotate at a pivot relative to the chassis;
a drive element supported by the chassis, the drive element being free to translate relative to the chassis along a second axis, the second axis being parallel with the first axis;
means for transferring rotation of the arm to rotation of the lever; and
means for transferring rotation of the lever to translate the drive element.

17. The force transmission mechanism of claim 16, wherein:
the shaft comprises an elongate tube having a first end supported by the chassis and a second end opposite from the first end;
an end effector is coupled to the second end of the elongate tube;
the drive element extends through the elongate tube to transfer a force applied at the first end of the drive element to the end effector; and
the drive element is configured to translate along the second axis relative to the elongate tube to actuate the end effector.

18. The force transmission mechanism of claim 16, wherein the means for transferring rotation of the lever to translate the drive element comprises a collar on the drive element and a slot on the lever engaged with the collar.

19. The force transmission mechanism of claim 16, wherein a first lever arm of the lever and a second lever arm of the lever intersect at a ninety-degree angle at a pivot that supports the lever on the chassis.

20. The force transmission mechanism of claim 16, wherein:
- the lever comprises a first lever arm, a second lever arm, and a third lever arm;
- the first lever arm extends between a pivot of the lever and a first end of the lever;
- the second lever arm extends between the pivot of the lever and a second end of the lever; and
- the third lever arm extends from the pivot of the lever opposite the second lever arm.

* * * * *